United States Patent
Seeber et al.

(10) Patent No.: US 6,265,218 B1
(45) Date of Patent: Jul. 24, 2001

(54) PLASMIDS WITHOUT A SELECTION MARKER GENE

(75) Inventors: Stefan Seeber, Penzburg; Rudiger Ruger, Huglfing, both of (DE)

(73) Assignee: Roche Diagnostics GmbH, Penzberg (DE)

( * ) Notice: Subject to any disclaimer, the term of this patent is extended or adjusted under 35 U.S.C. 154(b) by 0 days.

(21) Appl. No.: 08/793,618

(22) PCT Filed: Jul. 31, 1995

(86) PCT No.: PCT/EP95/03027

§ 371 Date: Jun. 10, 1997

§ 102(e) Date: Jun. 10, 1997

(87) PCT Pub. No.: WO96/05297

PCT Pub. Date: Feb. 22, 1996

(30) Foreign Application Priority Data

Aug. 11, 1994 (DE) ................................................ 44 28 402

(51) Int. Cl.⁷ .............................. C12N 15/00; C12N 5/00
(52) U.S. Cl. ........................ 435/455; 435/325; 435/320.1
(58) Field of Search ........................... 514/44; 435/320.1, 435/172.3, 69.2, 455, 325

(56) References Cited

U.S. PATENT DOCUMENTS

| | | | | |
|---|---|---|---|---|
| 4,931,373 | * | 6/1990 | Kawasaki et al. | 435/69.2 |
| 5,650,308 | * | 7/1997 | Baum | 435/172.3 |
| 5,670,488 | * | 9/1997 | Gregory et al. | 514/44 |
| 5,763,270 | | 6/1998 | Eastman et al. | 435/320.1 |

FOREIGN PATENT DOCUMENTS

| | | | |
|---|---|---|---|
| WO 92/20808 | * | 11/1992 | (WO) . |
| WO 93/01283 | * | 1/1993 | (WO) . |
| 9409127 | | 4/1994 | (WO) . |
| 9525800 | | 9/1995 | (WO) . |

OTHER PUBLICATIONS

"RNA Polymerase Idling and Clearance in gal Promoters: Use of Supercoiled Minicircle DNA Template Made In Vivo", Proc. Natl. Acad. Sci. USA, Vo. 90, pp. 472–476, (1993), Choy et al.

"Correction of the Ion Transport Defect in Cystic Fibrosis Transgenic Mice by Gene Therapy", Nature, vol. 362, pp. 250–255, (1993), Hyde et al.

"The Cycliation of Linear DNA in *Escherichia coli* by Site–Specific Recombination", Gene, vol. 70, pp. 331–341, (1988), Sauer et al.

"Selective Binding of *Escherichia coli* RNA Polymerase to Topoiomers of Minicircles Carrying the TAC16 and TAC17 Promoters", The Journal of Biological Chemistry, vol. 269, pp. 13511–13521, (1994), Su et al.

Rochat T. (Schweizerische Medizinische Wochenschrift 127 (5) 1997, 148–157), Abstract only.*

Report and Recommendations of the Panel to Assess the NIH Investment in Research on Gene Therapy, Dec. 1995.*

Crystal et al. Science vol 270, Oct. 20, 1995.*

Kolata et al. New York Times, Tuesday, Jul. 25, 1995.*

* cited by examiner

Primary Examiner—Deborah Crouch
(74) Attorney, Agent, or Firm—Fulbright & Jaworski, LLP (57) ABSTRACT

The use of a circular vector DNA to produce a pharmaceutical agent for the treatment of mammals or humans by gene therapy wherein the vector DNA contains a selection marker gene and a DNA sequence that is heterologous for the vector which causes a modulation, correction or activation of the expression of an endogenous gene or the expression of a gene introduced into the cells of the mammal or the human by the vector DNA which is characterized in that the vector nucleic acid a) is amplified under selection pressure and cleaved in such a way that the selection marker gene and the heterologous DNA are present on separate DNA fragments, b) the DNA fragment which contains the heterologous DNA or both fragments are recircularized to form vectors, c) the DNA fragments are separated before or after the recircularization d) the recircularized DNA fragment which contains the heterologous DNA is isolated and e) the recircularized DNA fragment obtained in this manner is used to produce the pharmaceutical agent.

5 Claims, 1 Drawing Sheet

PLASMIDS WITHOUT A SELECTION MARKER GENE

RELATED APPLICATION

This application claims priority from PCT Application PCT/EP95/03027 filed Jul. 31, 1995.

FIELD OF THE INVENTION

The invention concerns the use of vector DNA without a selection marker gene in gene therapy as well as the use of these vectors for the production of pharmaceutical agents for gene therapy.

BACKGROUND OF THE INVENTION

The gene therapy of somatic cells can be carried out for example using retroviral vectors, other viral vectors or by non-viral gene transfer (for review cf. T. Friedmann (1989) (1), Morgan (1993)(2)).

SUMMARY OF THE INVENTION

Delivery systems that are suitable for gene therapy are for example retroviruses (Mulligan, R. C. (1991)(3)), adeno associated virus (McLughlin (1988)(4)), vaccinia virus, (Moss et al. (1987 )(5)), bovine papilloma virus, (Rasmussen et al. (1987)(6)) or viruses from the herpes virus group such as the Epstein Barr virus (Margolskee et al. (1988)(7)) or herpes simplex virus.

Non-viral delivery systems are also known. "Naked" nucleic acid, preferably DNA, is usually used for this or nucleic acid together with an auxiliary substance such as e.g. with transfer reagents (liposomes, dendromers, polylysine-transferring conjugates (Wagner et al. (1990)(14), Felgner et al. (1987)(8)).

In order to provide the nucleic acid that can be used for gene therapy in a therapeutic amount, it is necessary to multiply these nucleic acids before the therapeutic application. This involves at least one selection step which utilizes a marker gene located on the nucleic acid and its gene product. Common selection markers are for example ampicillin, chloramphenicol, erythromycin, kanamycin, neomycin and tetracycline (Davies et al. (1978)(9)).

Several protocols for gene therapy are already known which are either still at the stage of animal experiments (Alton et al. (1993)(15); WO 93/1224 (10); Hyde et al. (1993)(16), Debs et al. (1991)(17)) or are already in clinical trials on patients (Nabel (1993)(18), (1994)(19)). A vector based on pBR322 or pUC18/19 is usually used in these protocols which carries an ampicillin resistance gene as the bacterial selection marker.

When nucleic acids are administered in a gene therapy treatment bacteria present in the respiratory and digestive tract and on the skin may take up the nucleic acids. However, when the marker is an active antibiotic-resistance gene (AB$^R$ gene) this may produce an antibiotic resistance in the patient as an undesired side effect. This is particularly disadvantageous when cystic fibrosis is treated by gene therapy. In this case large amounts of vector nucleic acid are administered to the patient as plasmid DNA or as an aerosol using liposomes as a DNA transfer reagent (Alton et al. (1993) (15)).

Patients with a cystic fibrosis illness usually additionally suffer from bacterial lung infections with for example *Pseudomonas aeruginosa, Staphylococcus aureus, Haemophilus influenzae* which are usually treated by administering antibiotics such as penicillin. Hence a resistance of the patients to these antibiotics is disadvantageous.

The previously described protocols for CF gene therapy by means of CFTR plasmid/liposome conjugates and publications of in vitro or animal experiments use vectors based on pUC18/19 or pBR322 which contain the ampicillin resistance gene as the bacterial selection marker (Alton et al. (1993)(15); WO 93/1224 (10); Hyde et al. (1993) (16)).

The common *E. coli* vectors based on pUC or pBR with the ampicillin resistance gene (Nabel et al. (1993)(18); Lori et al. (1994) (20); Cotten et al. (1994) (21); Lew et al. (1994)(22) etc.) are also used in the other in vivo gene therapy protocols and publications of in vitro or animal model studies with naked DNA or DNA/transfer system conjugates.

The invention concerns the use of a circular vector DNA to produce a pharmaceutical agent for the treatment of mammals or humans by gene therapy in which the vector contains a selection marker gene and a DNA sequence that is heterologous for the vector which causes a modulation, correction or activation of the expression of an endogenous gene or the expression of a gene introduced into the cells of the mammal or the human by the vector DNA which is characterized in that the vector nucleic acid a) is amplified under selection pressure and cleaved in such a way that the said selection marker gene and the said heterologous DNA are present on separate DNA fragments, b) the DNA fragment which contains the said heterologous DNA or both fragments are recircularized to form vectors, c) the said DNA fragments are separated before or after the recircularization d) the recircularized DNA fragment which contains the said heterologous DNA is isolated and e) the recircularized DNA fragment obtained in this manner is used to produce the pharmaceutical agent.

The cleavage in step (a) is preferably carried out by means of restriction endonucleases. In this case it is recircularized by adding ligase (step b). It is also preferred to carry out the cleavage and recircularization in one step by recombination with site-specific recombinase systems (SSR).

The use of site-specific recombinase systems (SSR systems) enables the AB$^R$ gene to be separated in an elegant manner from the remaining part of the vector (plasmid origin of replication and insert) if the specific recombination sites are placed correctly. For this purpose two specific recombination sites must be incorporated upstream and downstream of the AB$^R$ gene. If an SSR is added, this leads to a specific recombination between both recombination sites by which means the DNA pieces between the recombination sites are separated. In this manner two ring-like molecules are formed (one with the AB$^R$ gene and one with the insert and the plasmid origin of replication) each of which carries one recombination site.

It is essential that the DNA is recircularized again after deletion of the vector part (by ligase or recombinase), since circular DNA can be transfected with a higher efficiency than linear DNA (Chen and Okayama (1987) (37)) and has a longer half-life in the blood or in the target cell i.e. is less susceptible to nuclease action.

The two circular molecules formed in this manner can be separated from one another by chromatographic methods. The larger the difference in the size between the two molecules, the more effective is the separation. The circular therapeutic DNA obtained now only contains the therapeutically active gene plus necessary regulatory elements in order to ensure a gene expression in the human target cells as well as, for technical reasons, the E. coli plasmid origin of replication which, however, does not interfere at all. The interfering $AB^R$ gene is deleted.

The site-specific recombination can be carried out in vivo as well as in vitro. In the case of the in vivo site-specific recombination an SSR gene integrated into the host cell DNA (or F episome) is induced, the gene product formed, the SSR, carries out the specific recombination reaction in vivo on the therapeutic plasmid which is additionally present in the cell. The recombination products are isolated from the cell and separated in chromatographic processing steps. In order to carry out the site-specific recombination in vitro, purified SSR is added to the therapeutic plasmid isolated by conventional methods. After the recombination is completed the circular final products are separated from one another by chromatographic process steps.

In principle three systems are available as SSR:
1. The SSR systems of lysogenic phages:
e.g. the cre/lox system of the bacteriophage P1 (Sauer and Henderson (1988) (44); Baubonis (1993) (46)) the λint system of the bacteriophage λ (Landy et al. (1989) (42)) or the Gin system of the bacteriophage Mu (Klippel et al. (1993) (41)).
2. The SSR systems of the yeast plasmid 2 µA and analogous plasmids from other yeast strains:
e.g. the "FLP/FRT" system of the 2 µg episome from *Saccharomyces cerevisiae* (Cox et al. (1983) (40)), the "R" SSR system of the episome pSR1 from *Zygosaccharomyces rouxi* (Matsuzaki et al. (1990) (43)), the SSR system of the episome pKD1 from *Kluyveromyces drosophilarium* (Chen et al. (1986) (38)) or the SSR system of the episome pKW1 from *Kluyveromyces waltii* (Chen et al. (1992) (39)).
3. The transposon-coded integrases:
e.g. the integrase of the transposon Tn3 (Stark et al. (1992) (45)).

For this the cre/lox system of the bacteriophage P1 is particularly preferably used (N. Sternberg et al. (1986) (34); B. Sauer and N. Henderson (1989) (35)). For this purpose the vector contains $lox^P$ sites at the 5' and 3' ends of the heterologous DNA. The recombination (corresponding cleavage and recircularization) is carried out by the cre gene product recombinase. Two circular plasmid fragments are formed (with and without heterologous DNA) which, if the difference in size is adequate, can for example be separated chromatographically. The vector is preferably composed in such a way that the size of the heterologous DNA component and that of the base vector component differs by more than 1.5-fold preferably 2-fold. The recircularization is essential since circular DNA can be transformed with higher efficiency and has a higher half-life in blood or the target cell than linear DNA (less sensitive to nucleases).

The pharmaceutical agent is preferably administered as an aerosol.

A vector DNA is particularly preferably used which can correct a defect gene, introduce an intact gene or be exchanged at the correct gene locus. A vector DNA within the meaning of the invention is understood as a non-viral DNA molecule based on a prokaryotic plasmid. This DNA molecule additionally contains the DNA to be transferred in the gene therapy method preferably an expressible gene.

Non-viral DNA within the sense of the invention is understood to mean that this DNA is not a component of an infectious viral particle and does not contain an intact viral genome. However, the non-viral DNA can contain viral sequences such as e.g. regulation sequences (e.g. promoter, enhancer), transcription stops or viral genes such as e.g. the herpes simplex Tk gene.

Such vector DNA is particularly preferably used for the treatment of cystic fibrosis in humans. A gene suitable for this is described for example in WO 91/02796 (11).

This also describes the production and use of vectors for the treatment of cystic fibrosis by gene therapy.

The DNA vectors are particularly suitable for those gene therapy treatments in which the vectors come into direct contact with surfaces in mammals or humans. Such surfaces are for example the respiratory and digestive tract as well as the surface of the skin.

The invention in addition concerns a circular vector DNA preparation in an amount of 300 to 500 µg plasmid (30 to 90 pmol) which contains a gene or gene fragment which causes the activation, modulation or correction of the expression of an endogenous cystic fibrosis gene (CFTR gene, cystic fibrosis trans membrane conductance regulator gene) in mammalian cells or contains a CFTR gene which, after mammalian cells have been transfected with the vector DNA, results in the expression of this gene which is characterized in that this vector a) is amplified under selection pressure and cleaved in such a way that the said selection marker gene and the said heterologous DNA are present on separate DNA fragments, b) the said DNA fragments are separated before or after the recircularization c) the DNA fragment which contains the said heterologous DNA or both fragments are recircularized to form a vector, d) the recircularized DNA fragment which contains the said heterologous DNA is isolated and e) the recircularized DNA fragment obtained in this manner is used to produce the pharmaceutical agent.

After isolation the vector DNA preparation can be lyophilized or stored in a buffer solution (e.g. TE buffer).

Nucleic acids which are suitable according to the invention can be produced according to processes as described for example in Sambrook et al. (1985) (47). It is, however, also possible to use anion exchange columns to separate the DNA from RNA and proteins (e.g. Qiagen plasmid purification kit).

An important application is the improved treatment of cystic fibrosis by gene therapy. Previously known methods for the treatment of cystic fibrosis are described for example in WO 91/2796 (11). A CFTR gene suitable for gene therapy is also described there.

Cystic fibrosis is a serious monogenetic, autosomally recessive hereditary disease with a frequency of 1/2500 births. It is characterized by a deficient electrolyte transport of the epithelial tissue membrane which leads to abnormalities in the function (dysfunction of exocrine glands) of the respiratory tract, pancreas (increased production and increased viscosity of the secretory product of mucous glands), sweat glands (increased electrolyte content in the sweat and concomitant loss of liquid and electrolyte) and gonads. Respiratory insufficiency due to an inadequate secretion of chloride ions into the bronchial mucous by cells of the epithelium of the respiratory organ represents the most frequent clinical manifestation and cause of death in CF patients. It has been possible to clone the gene responsible and to characterise the gene product as a cyclic adenosine monophosphate (cAMP)-dependent chloride ion channel protein (CFTR=Cystic Fibrosis Transmembrane Conductance Regulator) (WO 91/2796 (11)). Knowledge of the pathophysiology of the disease, the structure and function of CFTR and mutations related to disorders of CFTR function nowadays enable various gene therapy approaches to be carried out in addition to the classical therapeutic methods which are not very effective.

Two methods have previously been used in announced and current clinical protocols for CF therapy. According to the first procedure, the CFTR gene is administered by means of inhalation of CFTR adenovirus vectors. Adenoviruses naturally infect the lung epithelium. First clinical successes have been achieved with this method but only for a short time period of a few weeks and with undesired toxic side effects (Zabner & Welsh (1993)(23)). The second method comprises introducing CFTR plasmids complexed with cationic liposomes into the respiratory tract by means of inhalation (Alton et al. (1993)(15)). In this case ca. 1 mg plasmid DNA/mouse is administered to mice; in the case of humans the plasmid doses are in the range of 100 $\mu$g–1 mg, preferably 300–500 $\mu$g plasmid/patient which corresponds to a number of ca. $5 \times 10^{13}$ DNA molecules at a plasmid size of 8.2 kb (Alton et al. (1993)(15); Whitsett et al. (1992)(24)). This application and dosage is also preferred according to the invention.

The lung epithelial cells can only take up a small amount of the introduced amount of plasmid. It is to be expected that the major portion of the plasmid is either exhaled or swallowed by the patient i.e. that a large amount reaches the environment (patients in hypobaric safety rooms) and the gastrointestinal tract of the patient.

Various bacterial genera are located in the lung flora some of which can manifest themselves as opportunistic pathogens e.g. Pseudomonads, Haemophilus, Enterobacteriaceae, Staphylococci etc. (Balows (1991)(12)).

A bacterial colonisation of the viscous, protein-rich secretion in the region of the respiratory passages which is greatly increased in CF patients, is a frequent cause of severe cases of bronchitis and pneumonia. CF patients are exposed above all to infections of the bronchi and lungs by *Haemophilus influenzae, Pseudomonas aeruginosa* and *Staphylococcus aureus* (Dodge et al. (1993)(25), FitzSimmons (1993)(25)) which is why they have to be subjected to antibiotic treatments in frequent succession.

The most important antibiotics for this are penicillin and its derivatives such as e.g. ampicillin (*H. influenzae*) and carbenicillin (*P. aeruginosa*, $\beta$-lactamase sensitive penicillin derivative, Davis et al. (1980)(27)). Due to widespread penicillin resistances in *Staphylococcus aureus* the $\beta$-lactamase resistant penicillin derivatives (methicillin, oxacillin, cephalosporin) are particularly important in this case.

In addition other pathogens are of importance in the case of lung infections e.g. Streptococcus pneumoniae (=pneumococci) the most common pathogenic agent causing bacterial pneumonia and Enterobacteriaceae (e.g. Klebsiella pneumoniae), penicillin being the most important therapeutic agent, particularly in the case of pneumococci (Davis et al. (1980)(27)).

Enterobacteriaceae and Enterococci are present among others in the gastrointestinal tract (Balows et al. (1991)(12)). Penicillin and its derivatives also play a central role in the treatment of intestinal infections which are caused by Enterobacter, *E. coli*, Serratia and *Streptococcus faecalis* (Davis et al. (1980)(27)).

Already in 1944 Avery described the uptake of high molecular DNA by Pneumococci from the medium, a process which is denoted as natural competence, plays an important role in bacterial evolution and is therefore widespread in the bacterial kingdom. Physiological transformation has been observed in the genera Haemophilus, Streptococcus, Staphylococcus, Neisseria, Bacillus and Acinetobacter (Davis et al. (1980)(27)). It can be assumed that Pseudomonads in which horizontal gene transfer is widespread are also able to take up high molecular DNA from the medium.

Bacteria of the natural flora of humans (respiratory tract, gastro-intestinal tract, skin, mucous membranes, eye etc.) are thus able to take up plasmid DNA. The DNA which is taken up can become integrated into the cell's own DNA (chromosome, plasmids) by recombinant events and thus come under the control of a promoter of the host i.e. be expressed.

When ca. 300–500 $\mu$g plasmid DNA/CF patient is administered (which corresponds to ca. $5 \times 10^{13}$ molecules at a plasmid size of 8.2 kb; Alton et al. (1993)(15)) there is a risk that antibiotic-resistant organisms may form among the bacteria of the lung flora and also in other regions of the body. As already stated, the production of antibiotic resistances and especially an ampicillin resistance ($\beta$-lactamase) is particularly disastrous for CF patients who suffer especially from bacterial lung infections and have to be continuously co-treated with antibiotics, in particular because the methods of gene therapy previously used still do not result in complete healing or a persistent correction.

In addition it is not possible to rule out that the ampicillin resistance gene introduced with the CFTR plasmid may become integrated into the patient's DNA, be expressed there under the control of one of the cell's promoters and the gene product be secreted actively or passively (e.g. cell lysis in the case of inflammatory reactions). The locally released $\beta$-lactamase could impede a penicillin therapy even in the case of a general bacterial infection.

The use according to the invention of DNA vectors without a selection marker gene is also advantageous in the treatment of AIDS (Lori et al. (1994)(20)) or cancer patients (Nabel et al. (1993)(18)) by gene therapy, since in both cases the patients are usually immuno-suppressed by the clinical syndrome itself (in the case of AIDS) or by therapy with chemotherapeutic agents or by radiotherapy (in the case of cancer). Bacterial infections in these patients can be prevented or brought under control by antibiotic treatment.

Apart from the lung and the respiratory tract, gene therapy approaches must also be considered for the treatment of other tissues under the aspects described above: Muscle tissue: gene therapeutic plasmids can for example be injected directly into muscle tissue (Ulmer et al. (1993)(28); Davis et al. (1993)(29); Lew et al. (1994)(22)) or into tumours (immuno-stimulation for tumor vaccination; Nabel et al. (1993)(18); San et al. (1993) (30)) for in vivo vaccination. Therapeutic plasmids have previously been injected in low doses for this purpose which is why the injected plasmid DNA only remained localized around the injection channel. In order to obtain systemic reactions it is not possible to avoid a larger dosage or a systemic administration of the therapeutic plasmids. This would then result in a spreading of the plasmid DNA in the blood system.

Blood system: For gene therapy in the liver it is possible to intravenously administer conjugates of plasmid DNA/polylysine/liver targeting groups (Chiou et al. (1994)(31)). This results in a spreading of the plasmid DNA in the blood system.

In both cases it is possible (muscle tissue, blood system) that the introduced plasmids reach bacterial foci, be taken up by these bacteria and impede antibiotic therapy when an infection breaks out.

Intestine: Conjugates of a therapeutic plasmid (e.g. with a tumor suppressor gene) can be introduced directly into the intestine for the gene therapy of colon cancer (Arenas et al. (1994)(32)). Gene delivery of, for example, genes which code for the LDL receptor via the intestinal mucous membrane is also under consideration. Introduced plasmids can transfer the antibiotic resistance gene to the bacteria of the gastro-intestinal tract.

Skin: Plasmid DNA can be taken up directly as a conjugate with liposomes into skin cells e.g. for the gene therapy of melanoma or haemophilia B (factor IX, X) (Alexander et al. (1994)(33)). In this manner it is possible for bacteria of the skin flora to obtain antibiotic resistances.

Eye: Persistent virus infections of the eye can be treated by gene therapy using therapeutic plasmids which involves the risk of transferring antibiotic resistances to the bacteria of the eye flora.

The invention is elucidated further by the following examples, the figure and the sequence protocol. A detailed description of the experimental conditions is included in J. Sambrook (1989)(13).

BRIEF DESCRIPTION OF THE FIGURE

SEQ ID NO:1 shows the DNA sequence of PCMV-CFTR.

SEQ ID NO:2–5 show DNA sequences of DNA linkers.

DESCRIPTION OF THE PREFERRED EMBODIMENT

The present invention is described with reference to the following examples.

EXAMPLE 1

Determination of the Uptake Rate of Plasmids and Production of Antibiotic Resistances by Bacteria of the Human Lung and Intestinal Flora It is intended to demonstrate that E. coli plasmid DNA, e.g. pUC18 or derivatives thereof, can be taken up by bacteria of other genera and that the ampicillin resistance gene can be expressed which leads to ampicillin-resistant clones. The probability of forming ampicillin-resistant microorganisms is determined by the uptake rate of plasmid DNA from the substrate and the rate of incorporation of the ampicillin resistance gene by non-homologous recombination into the chromosomal DNA of the host bacterium. Plasmids with alternative markers or with markers inactivated by stop codons (see above) no longer result in the development of resistance.

The experiments are carried out on the following bacterial species:

Gram-negative:
  Haemophilus influenzae
  Pseudomonas aeruginosa
  Klebsiella pneumoniae
  Escherichia coli (WT)
Gram-positive:
  Staphylococcus aureus
  Streptococcus pneumoniae For this various amounts of plasmid DNA are added under various conditions to cultures of the above-mentioned organisms.

Liquid cultures in nutrient medium are carried out using isotonic buffer (NaCl, $Mg^{2+}$, $Ca^{2+}$). Various concentrations of plasmid DNA (e.g. pUC18/$ap_R$ gene) are added to these cultures. After incubation for several hours while shaking, antibiotic is added. It is incubated further, plated out on agar containing antibiotic and a dilution series is carried out on agar which does not contain antibiotic. The number of living organisms is determined after incubation by counting and identifying or characterising the colonies obtained.

In detail for this a bacterial culture incubated overnight is centrifuged, the pellet is washed with phosphate-buffered saline solution (PBS), resuspended in 2% culture volume PBS and admixed with 200 ng plasmid DNA/ml. A dilution series is immediately plated out on plates without antibiotic. The suspension is slowly shaken at 37° C. and at various intervals (1, 2 and 4 h) dilution series are plated out with and without antibiotics (ampicillin 100 µg/ml) on standard I agar and incubated at 37° C. The $10^1$–$10^5$ dilutions are plated out on antibiotic plates and the $10^9$–$10^{10}$ dilutions are plated out on plates without selection. The transformed resistant cultures are counted the next day and related to the number of viable germs.

Alternatively a defined amount of plasmid and a defined germ count of bacteria are plated out on nutrient agar and incubated for several hours, antibiotics are added by spraying and the colonies obtained are counted and identified or characterized. It is also possible to apply a defined amount of plasmid and a defined germ count of bacteria to a nylon filter and to incubate the filters for several hours on nutrient agar. Subsequently the filters are transferred onto nutrient agar containing antibiotic, incubated and the colonies obtained are counted and identified or characterized.

EXAMPLE 2

Construction and Amplification of Safety Vectors Based on pUC18 which no Longer Possess a Selection Marker.

The principle of the method is based on the restriction of the isolated therapeutic plasmid, separation of the small fragments containing the vector part (+resistance gene) and religation of the large fragment with the therapeutically active gene in several steps in vitro (restriction endonucleases+ligase) or in one step in vivo or in vitro (site-specific recombinases). The feasibility of the method was demonstrated using the vector pUC18 and the therapeutic plasmid pCMV-CFTR (Alton et al. (15)).

Figure 1:
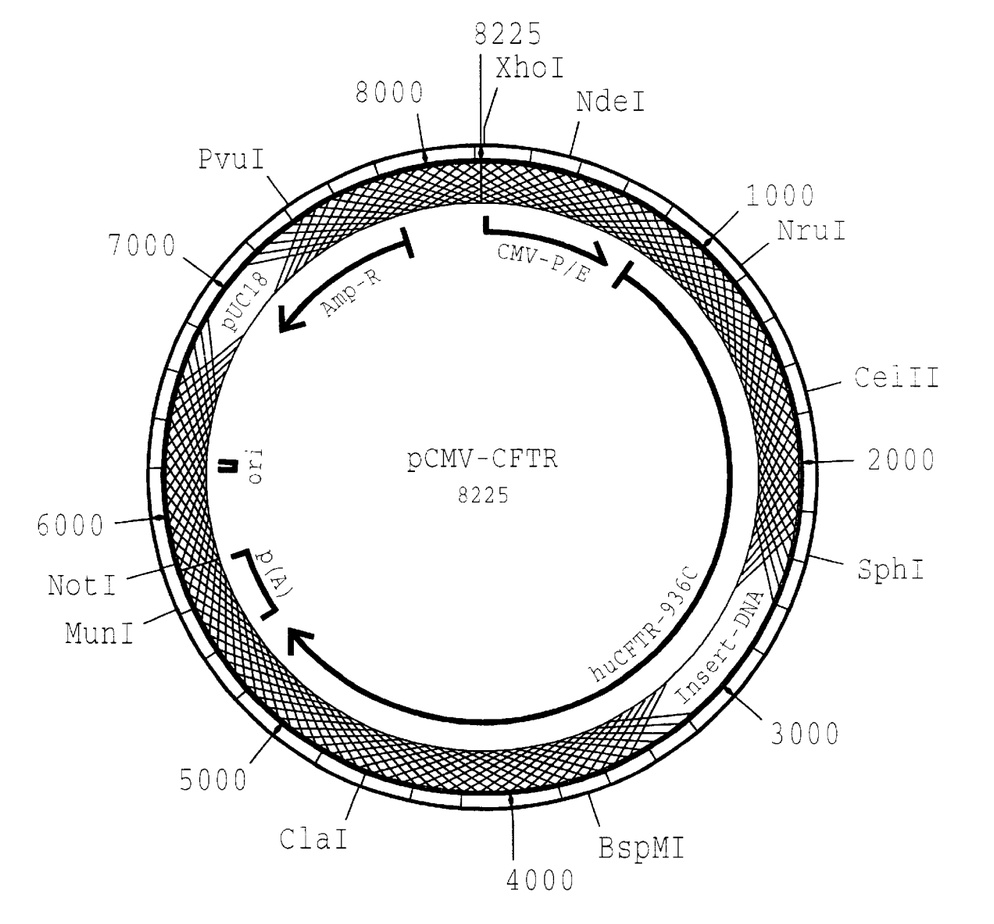
FIG. 1 shows the plasmid map of pCMV-CFTR.

The plasmid map of pCMV-CFTR is shown in FIG. 1, the DNA sequence is shown in SEQ ID NO:1.

Plasmid Construction

1. In order to facilitate the separation of the insert (containing the therapeutic gene) from the vector part, several linkers with restriction cleavage sites were incorporated distributed over the vector. PstI and PvuI were chosen as the restriction enzymes since they do not cut in the insert (CMV-CFTR) in the plasmid pCMV-CFTR chosen as an example. It is, however, also possible to use other enzymes which have the same property of not cutting in the insert. In addition linkers with more than one restriction cleavage site can also be used. In this example linkers with two restriction cleavage sites namely for PstI and PvuI were used.

Thus synthetic DNA linkers containing the recognition sequences of PvuI+PstI were incorporated into pUC18 in a defined sequence (5'PstI-PvuI in AatII and AflIII; 5'Pvu-PstI in AlwNI) into the singular AflIII, AlwNI and AatII cleavage sites using common laboratory techniques.

for AatII site: 5'PstI/PvuI/(AatII overhang) 5'-GCTGCAGCGATCGC (ACGT)-3'*) (SEQ ID NO:2)
for AflIII site: 5'-(AflIII overhang)/PstI/PvuI 5'-(CATG) CTGCAGCGATCGC-3'*) (SEQ ID NO:3)
for AlwNI site: 5'-PvuI/PstI/(AlwNI overhang) 5'-GCGATCGCTGCAG(CCA)-3'*) (SEQ ID NO:4)
*) Only one strand of the synthetic linker is shown.

The sequence is above all important for the AatII and the AlwNI cleavage site since this builds in additional safety which, apart from the physical separation, prevents the Amp$^R$ gene from religating with the insert. Therefore the double-stranded linkers must have corresponding overhangs for each of the enzyme cleavage sites in order to clone them in the right orientation or if the linkers are cloned via blunt ends, clones having the correct orientation must be sought after.

2. The polylinker of pUC18 was exchanged for a newly synthesized polylinker in order to firstly facilitate the cloning of the CMV-CFTR gene cassette and secondly to enable a clean separation of the vector and insert (=CMV-CFTR gene cassette).

The synthetic DNA polylinker contains the restriction cleavage sites in the following sequence: 5'-(HindIII)-PvuI-PstI-XhoI-SalI-XbaI-BamHI-SmaI-NotI-PstI-PvuI-(EcoRI).

5'-(AGCT)TCGATCGCTGCAGTCGACTCTAGAGGATCCCGGGCGGCCGCTGCAGCGATCG(AATT)-3'\*) (SEQ ID NO:5)

\*) Only one strand of the synthetic linker is shown. The parentheses mean that the polylinker has overhangs for the corresponding enzymes and can in this orientation be ligated in the correct orientation into pUC18 which had been cleaved with HindIII and EcoRI.

The vector that formed was named PUC-PP_1.

3. The 5.8 kb DNA fragment containing the CMV-CFTR gene cassette which was also cut out by means of a XhoI/NotI double digestion from pCMV-CFTR was inserted in the correct orientation between the XhoI and the NotI cleavage sites of pUC-PP_1 (addition of ligase). The plasmid that was formed was named pCMV-CFTR_PP2. When restricted with PvuI+PstI it disintegrates into fragments of sizes: 5.8 and 0.85, 0.55, 0.42, 0.36, 0.34, 0.12 kb.

Construction of the resistance-free plasmid a) Cleavage with restriction endonucleases pCMV-CFTR_PP2 was transformed in *E. coli*. *E. coli* (pCMV-CFTR_PP2) was fermented, disrupted and the plasmid DNA was purified by means of a QIAGEN® column according to the manufacturer's specification (QUIAGEN; Germany). The purified plasmid DNA was cleaved with PvuI (10 U/µg; 1 µg in 20 µl volume; according to the specification of the PvuI manufacturer). The DNA was then recleaved with PvuI+PstI (5 U/µg PvuI+10 U/µg PstI). The fragments were separated by a molecular sieve column and the much larger 5.8 kb fragment was separated by this means. The eluted 5.8 kb fragment was religated by means of T4 ligase (according to the specification of the manufacturer). The 5.8 kb recircularized DNA (1 mg DNA in 1 ml buffer) containing the CMV-CFTR gene cassette was again purified by means of a QIAGEN column and taken up in a small amount of buffer Tris HCl/EDTA buffer (10 mmol/Tris HCl, 0.1 mmol/l EDTA (pH=7.0).

b) Cleavage and recircularization by recombination ba) in vivo use of the cre/lox system for the recombinant deletion of the AB$^R$ gene:

The procedure was carried out similarly to the methods described by Sauer (1988) (44) via a cre-recombinase-mediated release of circular plasmids which were present integrated into large linear DNA molecules flanked by loxP sites. However, in these methods *E. coli* strains were used in which the cre-recombinase gene was present constitutively expressed. For the example described here the cre-recombinase gene must be present under the control of a strictly regulatable promoter.

For this purpose two 34 bp loxP recombination sites were incorporated upstream and downstream of the ampicillin resistance gene into the therapeutic plasmid pCMV-CFTR.

The plasmid was named pCMV-CFTR_2loxP. The plasmid obtained pCMV-CFTR_2loxP was cloned in *E. coli* XL1-Blue_λimm434nin5_Xi-T5-cre (construction analogous to Sauer (1988) (44)) which contains the lysogenic phage λ containing the cre-recombinase gene under the control of the strictly regulatable T5 promoter (Bujard et al. (1987) (36)) as well as a lac1$^q$-gene (F-episomally coded).

bb) Culture and in vivo recombination

*E. coli* Xl1-Blue_λimm434nin5_X1-T5-cre (pCMV-CFTR_2loxP) was cultured in LB medium containing 100 µg/ml ampicillin. The T5 promoter was induced by addition of 5 mM IPTG and thus the expression of the cre-recombinase gene was switched on. The cre-recombinase carried out an in vivo recombination of the two loxP sites in PCMV-CFTR_2loxP. As a result the plasmid PCMV-CFTR_loxP was converted into two circular plasmids of greatly differing size. Subsequently the *E. coli* cells were harvested, disrupted and the mixture of circular plasmids was isolated. The mixture was composed of unchanged pCMV-CFTR-2loxP, the circular Amp$^R$ gene containing a loxP site and the desired final product (the circular DNA containing the therapeutic insert+a loxP site+the pUC origin of replication). Subsequently the circular DNA molecules of various sizes were separated by means of chromatographic methods and the desired final product was taken up in citrate buffer (pH=7.0).

Since the cre/lox recombination can proceed in both directions, it is important that the reaction period or the time of harvest after IPTG induction is optimized. Since the T5 promoter system is present not completely repressed even in lac1$^q$ strains, there is always a low expression of the cre-recombinase gene and thus a low level of recombinations. By placing one of the two loxp sites between the Amp$^R$ gene and the origin of replication it can, however, be ensured that the cremediated recombinations only lead to the formation of constructs which cannot replicate and no longer mediate ampicillin resistance. They are rapidly lost during the replication cycles under a selection pressure by ampicillin addition.

LIST OF REFERENCES (1) T. Friedmann, Science 244 (1989) 1275
(2) Morgan 1993, RAC DATA MANAGEMENT Report, June 1993
(3) Mulligan, R. C. (1991) in Nobel Symposium 8: Ethiology of human disease at the DNA level (Lindsten, J. and Pattersun Editors), pages 143–189 Raven Press
(4) McLughlin, J. Virol. 62 (1988) 1963
(5) Moss et al., Ann. Rev. Immunol. 5 (1987) 305
(6) Rasmussen et al., Methods Enzymol. 139 (1987) 642
(7) Margolskee et al., Mol. Cell. Biol. 8 (1988) 2937
(8) Felgner et al., Proc. Natl. Acad. Sci. USA 84 (1987) 7413
(9) Davies et al., Ann. Rev. Microbiol. 32 (1978) 469
(10) WO 93/1224
(11) WO 91/02796
(12) Balows, Manual of Clinical Microbiology (1991)
(13) J. Sambrook, Molecular Cloning, Second Edition (1989) Cold Spring Harbor Laboratory Press, New York
(14) Wagner et al., Proc. Natl. Acad. Sci. USA 87 (1990) 3410–3414
(15) Alton et al., Nature Genetics 5 (1993) 135–142
(16) Hyde et al., Nature 362 (1993) 250–255
(17) Debs et al., WO 92/1224, A1, 17.12.91 US
(18) Nabel et al., Proc. Natl. Acad. Sci. USA (1993) 11307–11311
(19) Nabel et al., Human Gene Therapy 5 (1994) 79–92
(20) Lori et al., Gene Therapy 1 (1994) 27–31

(21) Cotten et al., J. of Cellular Biochemistry 18A (1994) Abstract DZ002
(22) Lew et al., J. of Cellular Biochemistry 18A (1994) Abstract DZ120
(23) Zabner & Welsh, Cell 75 (1993) 207–216
(24) Whisett et al., Nature Genetics 2 (1992) 13–20
(25) Dodge et al., Cystic Fibrosis, Current Topics, Vol. 1 (1993), John Wiley & Sons
(26) FitzSimmons, S. C., The Journal of Pediatrics 122 (1993) 1–9
(27) Davis et al., Microbiology, Third Edition (1980) Harper International Edition
(28) Ulmer et al., Science 259 (1993) 1745–1749
(29) Davies et al., Human Gene Therapy 4 (1993) 733–740
(30) San et al., Human Gene Therapy 4 (1993) 781–788
(31) Chiou et al., J. of Cellular Biochemistry 18A (1994) Abstract DZ109
(32) Arenas et al., J. of Cellular Biochemistry 18A (1994) Abstract DZ101
(33) Alexander et al., J. of Cellular Biochemistry 18A (1994) Abstract DZ400
(34) Sternberg, N., et al., J. Mol. Biol. 187 (1986) 197–212
(35) Sauer, B., Henderson, N., NAR 17 (1989) 147–161
(36) Bujard, H., et al., Methods in Enzymology 155 (1987) 416–443
(37) Chen, C. and Okayama, Mol. and Cell. Biol. 7 (1987) 2745–2752
(38) Chen, X. J., et al., NAR 14 (1986) 4471–4481
(39) Chen, X. J., et al., J. of Gen. Microbiol. 138 (1992) 337–345
(40) Cox, M. M., Proc. Natl. Acad. Sci. USA 89 (1983) 4223–4227
(41) Klippel, A., et al., The EMBO Journal 12 (1993) 1047–1057
(42) Landy, A., Ann. Rev. Biochem. 58 (1989) 913–949
(43) Matsuzaki, H., et al., J. of Bacteriol. 172 (1990) 610–618
(44) Sauer, B., and Henderson, N., Gene 70 (1988) 331–341
(45) Stark, W. M., et al., TIG 8 (1992) 432–439
(46) Baubonis et al., NAR 21 (1993) 2025–2029
(47) Sambrook et al., CSH Press (1985), Cold Spring Harbor, 1.21–1.52

What is claimed is:

1. A method for making a plasmid comprising a DNA sequence encoding a product comprising:
   (i) introducing a heterologous DNA sequence encoding a product operatively linked to a promoter into a plasmid, said plasmid further comprising a DNA sequence encoding an antibiotic resistance selection marker operatively linked to a promoter and wherein restriction enzyme cleave sites separate the two DNA sequences;
   (ii) amplifying said plasmid;
   (iii) cleaving by restriction enzymes said amplified plasmid to form two linear fragments, the first of which comprises said heterologous DNA sequence operatively linked to a promoter, the second of which comprises said DNA sequence encoding said selection marker operatively linked to a promoter;
   (iv) circularizing each of said fragments to form two plasmids, the first of which comprises said heterologous DNA sequence operatively linked to a promoter and lacking said DNA sequence encoding a selection marker, the second of which comprises said DNA sequence encoding said selection marker operatively linked to a promoter and lacking said heterologous DNA sequence;

(v) separating the plasmids obtained in (iv); and (vi) isolating the plasmid comprising the heterologous DNA sequence encoding a product operatively linked to a promoter.

2. The method according to claim 1, wherein said heterologous DNA sequence encodes a cystic fibrosis trans membrane conductance regulator (CFTR).

3. A plasmid comprising a heterologous DNA sequence encoding a product operatively linked to a promoter, wherein said plasmid lacks a DNA sequence encoding an antibiotic resistance marker produced according to claim 1.

4. A plasmid comprising a heterologous DNA sequence encoding a cystic fibrosis trans membrane conductance regulator (CFTR) operatively linked to a promoter, wherein said plasmid lacks a heterologous DNA sequence encoding an antibiotic resistance marker produced according to claim 2.

5. A method for producing a cell comprising a DNA sequence encoding a wild type CFTR, comprising transfecting cultured mammalian cells which lack expression of functional CFTR with the plasmid of claim 4, wherein the DNA sequence encoding a wild type CFTR is expressed.

* * * * *

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
        (A) LENGTH: 8225 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 1:

GGCCGCCGCG GCCTCGAGGA GCTTGGCCCA TTGCATACGT TGTATCCATA TCATAATATG      60

TACATTTATA TTGGCTCATG TCCAACATTA CCGCCATGTT GACATTGATT ATTGACTAGT     120

TATTAATAGT AATCAATTAC GGGGTCATTA GTTCATAGCC CATATATGGA GTTCCGCGTT     180

ACATAACTTA CGGTAAATGG CCCGCCTGGC TGACCGCCCA ACGACCCCCG CCCATTGACG     240

TCAATAATGA CGTATGTTCC CATAGTAACG CCAATAGGGA CTTTCCATTG ACGTCAATGG     300

GTGGAGTATT TACGGTAAAC TGCCCACTTG GCAGTACATC AAGTGTATCA TATGCCAAGT     360

ACGCCCCCTA TTGACGTCAA TGACGGTAAA TGGCCCGCCT GGCATTATGC CCAGTACATG     420

ACCTTATGGG ACTTTCCTAC TTGGCAGTAC ATCTACGTAT TAGTCATCGC TATTACCATG     480

GTGATGCGGT TTTGGCAGTA CATCAATGGG CGTGGATAGC GGTTTGACTC ACGGGGATTT     540

CCAAGTCTCC ACCCCATTGA CGTCAATGGG AGTTTGTTTT GGCACCAAAA TCAACGGGAC     600

TTTCCAAAAT GTCGTAACAA CTCCGCCCCA TTGACGCAAA TGGGCGGTAG GCGTGTACGG     660

TGGGAGGTCT ATATAAGCAG AGCTCGTTTA GTGAACCGTC AGATCGCCTG GAGACGCCAT     720

CCACGCTGTT TTGACCTCCA TAGAAGACAC CGGGACCGAT CCAGCCTCCC CGGCTAGGGT     780

CGACGGTACC CGAGAGACCA TGCAGAGGTC GCCTCTGGAA AAGGCCAGCG TTGTCTCCAA     840

ACTTTTTTTC AGCTGGACCA GACCAATTTT GAGGAAAGGA TACAGACAGC GCCTGGAATT     900

GTCAGACATA TACCAAATCC CTTCTGTTGA TTCTGCTGAC AATCTATCTG AAAAATTGGA     960

```
AAGAGAATGG GATAGAGAGC TGGCTTCAAA GAAAAATCCT AAACTCATTA ATGCCCTTCG   1020

GCGATGTTTT TTCTGGAGAT TTATGTTCTA TGGAATCTTT TTATATTTAG GGGAAGTCAC   1080

CAAAGCAGTA CAGCCTCTCT TACTGGGAAG AATCATAGCT TCCTATGACC CGGATAACAA   1140

GGAGGAACGC TCTATCGCGA TTTATCTAGG CATAGGCTTA TGCCTTCTCT TTATTGTGAG   1200

GACACTGCTC CTACACCCAG CCATTTTTGG CCTTCATCAC ATTGGAATGC AGATGAGAAT   1260

AGCTATGTTT AGTTTGATTT ATAAGAAGAC TTTAAAGCTG TCAAGCCGTG TTCTAGATAA   1320

AATAAGTATT GGACAACTTG TTAGTCTCCT TTCCAACAAC CTGAACAAAT TTGATGAAGG   1380

ACTTGCATTG GCACATTTCG TGTGGATCGC TCCTTTGCAA GTGGCACTCC TCATGGGGCT   1440

AATCTGGGAG TTGTTACAGG CGTCTGCCTT CTGTGGACTT GGTTTCCTGA TAGTCCTTGC   1500

CCTTTTTCAG GCTGGGCTAG GGAGAATGAT GATGAAGTAC AGAGATCAGA GAGCTGGGAA   1560

GATCAGTGAA AGACTTGTGA TTACCTCAGA ATGATTGAA AACATCCAAT CTGTTAAGGC    1620

ATACTGCTGG GAAGAAGCAA TGGAAAAAAT GATTGAAAAC TTAAGACAAA CAGAACTGAA   1680

ACTGACTCGG AAGGCAGCCT ATGTGAGATA CTTCAATAGC TCAGCCTTCT TCTTCTCAGG   1740

GTTCTTTGTG GTGTTTTTAT CTGTGCTTCC CTATGCACTA ATCAAAGGAA TCATCCTCCG   1800

GAAAATATTC ACCACCATCT CATTCTGCAT TGTTCTGCGC ATGGCGGTCA CTCGGCAATT   1860

TCCCTGGGCT GTACAAACAT GGTATGACTC TCTTGGAGCA ATAAACAAAA TACAGGATTT   1920

CTTACAAAAG CAAGAATATA AGACATTGGA ATATAACTTA ACGACTACAG AAGTAGTGAT   1980

GGAGAATGTA ACAGCCTTCT GGGAGGAGGG ATTTGGGGAA TTATTTGAGA AAGCAAAACA   2040

AAACAATAAC AATAGAAAAA CTTCTAATGG TGATGACAGC CTCTTCTTCA GTAATTTCTC   2100

ACTTCTTGGT ACTCCTGTCC TGAAAGATAT TAATTTCAAG ATAGAAAGAG ACAGTTGTT    2160

GGCGGTTGCT GGATCCACTG GAGCAGGCAA GACTTCACTT CTAATGATGA TTATGGGAGA   2220

ACTGGAGCCT TCAGAGGGTA AAATTAAGCA CAGTGGAAGA ATTTCATTCT GTTCTCAGTT   2280

TTCCTGGATT ATGCCTGGCA CCATTAAAGA AAATATCATC TTTGGTGTTT CCTATGATGA   2340

ATATAGATAC AGAAGCGTCA TCAAAGCATG CCAACTAGAA GAGGACATCT CCAAGTTTGC   2400

AGAGAAAGAC AATATAGTTC TTGGAGAAGG TGGAATCACA CTGAGTGGAG GTCAACGAGC   2460

AAGAATTTCT TTAGCAAGAG CAGTATACAA AGATGCTGAT TTGTATTTAT TAGACTCTCC   2520

TTTTGGATAC CTAGATGTTT TAACAGAAAA AGAAATATTT GAAAGCTGTG TCTGTAAACT   2580

GATGGCTAAC AAAACTAGGA TTTTGGTCAC TTCTAAAATG GAACATTTAA AGAAAGCTGA   2640

CAAAATATTA ATTTTGCATG AAGGTAGCAG CTATTTTTAT GGGACATTTT CAGAACTCCA   2700

AAATCTACAG CCAGACTTTA GCTCAAAACT CATGGGATGT GATTCTTTCG ACCAATTTAG   2760

TGCAGAAAGA AGAAATTCAA TCCTAACTGA GACCTTACAC CGTTTCTCAT TAGAAGGAGA   2820

TGCTCCTGTC TCCTGGACAG AAACAAAAAA ACAATCTTTT AAACAGACTG GAGAGTTTGG   2880

GGAAAAAAGG AAGAATTCTA TTCTCAATCC AATCAACTCT ATACGAAAAT TTTCCATTGT   2940

GCAAAAGACT CCCTTACAAA TGAATGGCAT CGAAGAGGAT TCTGATGAGC CTTTAGAGAG   3000

AAGGCTGTCC TTAGTACCAG ATTCTGAGCA GGGAGAGGCG ATACTGCCTC GCATCAGCGT   3060

GATCAGCACT GGCCCCACGC TTCAGGCACG AAGGAGGCAG TCTGTCCTGA ACCTGATGAC   3120

ACACTCAGTT AACCAAGGTC AGAACATTCA CCGAAAGACA ACAGCATCCA CACGAAAAGT   3180

GTCACTGGCC CCTCAGGCAA ACTTGACTGA ACTGGATATA TATTCAAGAA GGTTATCTCA   3240

AGAAACTGGC TTGGAAATAA GTGAAGAAAT TAACGAAGAA GACTTAAAGG AGTGCCTTTT   3300

TGATGATATG GAGAGCATAC CAGCAGTGAC TACATGGAAC ACATACCTTC GATATATTAC   3360
```

```
TGTCCACAAG AGCTTAATTT TTGTGCTAAT TTGGTGCTTA GTAATTTTTC TGGCAGAGGT    3420

GGCTGCTTCT TTGGTTGTGC TGTGGCTCCT TGGAAACACT CCTCTTCAAG ACAAAGGGAA    3480

TAGTACTCAT AGTAGAAATA ACAGCTATGC AGTGATTATC ACCAGCACCA GTTCGTATTA    3540

TGTGTTTTAC ATTTACGTGG GAGTAGCCGA CACTTTGCTT GCTATGGGAT TCTTCAGAGG    3600

TCTACCACTG GTGCATACTC TAATCACAGT GTCGAAAATT TTACACCACA AAATGTTACA    3660

TTCTGTTCTT CAAGCACCTA TGTCAACCCT CAACACGTTG AAAGCAGGTG GGATTCTTAA    3720

TAGATTCTCC AAAGATATAG CAATTTTGGA TGACCTTCTG CCTCTTACCA TATTTGACTT    3780

CATCCAGTTG TTATTAATTG TGATTGGAGC TATAGCAGTT GTCGCAGTTT ACAACCCTA    3840

CATCTTTGTT GCAACAGTGC CAGTGATAGT GGCTTTTATT ATGTTGAGAG CATATTTCCT    3900

CCAAACCTCA CAGCAACTCA AACAACTGGA ATCTGAAGGC AGGAGTCCAA TTTTCACTCA    3960

TCTTGTTACA AGCTTAAAAG GACTATGGAC ACTTCGTGCC TTCGGACGGC AGCCTTACTT    4020

TGAAACTCTG TTCCACAAAG CTCTGAATTT ACATACTGCC AACTGGTTCT TGTACCTGTC    4080

AACACTGCGC TGGTTCCAAA TGAGAATAGA ATGATTTTT GTCATCTTCT TCATTGCTGT    4140

TACCTTCATT TCCATTTTAA CAACAGGAGA AGGAGAAGGA AGAGTTGGTA TTATCCTGAC    4200

TTTAGCCATG AATATCATGA GTACATTGCA GTGGGCTGTA AACTCCAGCA TAGATGTGGA    4260

TAGCTTGATG CGATCTGTGA GCCGAGTCTT TAAGTTCATT GACATGCCAA CAGAAGGTAA    4320

ACCTACCAAG TCAACCAAAC CATACAAGAA TGGCCAACTC TCGAAAGTTA TGATTATTGA    4380

GAATTCACAC GTGAAGAAAG ATGACATCTG GCCCTCAGGG GGCCAAATGA CTGTCAAAGA    4440

TCTCACAGCA AAATACACAG AAGGTGGAAA TGCCATATTA GAGAACATTT CCTTCTCAAT    4500

AAGTCCTGGC CAGAGGGTGG GCCTCTTGGG AAGAACTGGA TCAGGGAAGA GTACTTTGTT    4560

ATCAGCTTTT TTGAGACTAC TGAACACTGA AGGAGAAATC CAGATCGATG GTGTGTCTTG    4620

GGATTCAATA ACTTTGCAAC AGTGGAGGAA AGCCTTTGGA GTGATACCAC AGAAAGTATT    4680

TATTTTTTCT GGAACATTTA GAAAAAACTT GGATCCCTAT GAACAGTGGA GTGATCAAGA    4740

AATATGGAAA GTTGCAGATG AGGTTGGGCT CAGATCTGTG ATAGAACAGT TCCTGGGAA    4800

GCTTGACTTT GTCCTTGTGG ATGGGGGCTG TGTCCTAAGC CATGGCCACA AGCAGTTGAT    4860

GTGCTTGGCT AGATCTGTTC TCAGTAAGGC GAAGATCTTG CTGCTTGATG AACCCAGTGC    4920

TCATTTGGAT CCAGTAACAT ACCAAATAAT TAGAAGAACT CTAAAACAAG CATTTGCTGA    4980

TTGCACAGTA ATTCTCTGTG AACACAGGAT AGAAGCAATG CTGGAATGCC AACAATTTTT    5040

GGTCATAGAA GAGAACAAAG TGCGGCAGTA CGATTCCATC CAGAAACTGC TGAACGAGAG    5100

GAGCCTCTTC CGGCAAGCCA TCAGCCCCTC CGACAGGGTG AAGCTCTTTC CCCACCGGAA    5160

CTCAAGCAAG TGCAAGTCTA AGCCCCAGAT TGCTGCTCTG AAAGAGGAGA CAGAAGAAGA    5220

GGTGCAAGAT ACAAGGCTTT AGAGAGCAGC ATAAATGTTG ACATGGGACA TTTGCTCATG    5280

GAATTGGAGC TCGTCGACTC TAGAGGATCC CCGGGCGAGC TCGAATTCAA GCTTGGGATC    5340

TTTGTGAAGG AACCTTACTT CTGTGGTGTG ACATAATTGG ACAAACTACC TACAGAGATT    5400

TAAAGCTCTA AGGTAAATAT AAAATTTTTA AGTGTATAAT GTGTTAAACT ACTGATTCTA    5460

ATTGTTTGTG TATTTTAGAT TCACAGTCCC AAGGCTCATT TCAGGCCCCT CAGTCCTCAC    5520

AGTCTGTTCA TGATCATAAT CAGCCATACC ACATTTGTAG AGGTTTTACT TGCTTTAAAA    5580

AACCTCCCAC ACCTCCCCCT GAACCTGAAA CATAAAATGA ATGCAATTGT TGTTGTTAAC    5640

TTGTTTATTG CAGCTTATAA TGGTTACAAA TAAAGCAATA GCATCACAAA TTTCACAAAT    5700
```

-continued

```
AAAGCATTTT TTTCACTGCA TTCTAGTTGT GGTTTGTCCA AACTCATCAA TGTATCTTAT    5760

CATGTCTGGA TCCCCGGGTA CCGAGCTCGA ATTAGCGGCC GCTAATTCGT AATCATGGTC    5820

ATAGCTGTTT CCTGTGTGAA ATTGTTATCC GCTCACAATT CCACACAACA TACGAGCCGG    5880

AAGCATAAAG TGTAAAGCCT GGGGTGCCTA ATGAGTGAGC TAACTCACAT TAATTGCGTT    5940

GCGCTCACTG CCCGCTTTCC AGTCGGGAAA CCTGTCGTGC CAGCTGCATT AATGAATCGG    6000

CCAACGCGCG GGGAGAGGCG GTTTGCGTAT TGGGCGCTCT TCCGCTTCCT CGCTCACTGA    6060

CTCGCTGCGC TCGGTCGTTC GGCTGCGGCG AGCGGTATCA GCTCACTCAA AGGCGGTAAT    6120

ACGGTTATCC ACAGAATCAG GGGATAACGC AGGAAAGAAC ATGTGAGCAA AAGGCCAGCA    6180

AAAGGCCAGG AACCGTAAAA AGGCCGCGTT GCTGGCGTTT TTCCATAGGC TCCGCCCCCC    6240

TGACGAGCAT CACAAAAATC GACGCTCAAG TCAGAGGTGG CGAAACCCGA CAGGACTATA    6300

AAGATACCAG GCGTTTCCCC CTGGAAGCTC CCTCGTGCGC TCTCCTGTTC CGACCCTGCC    6360

GCTTACCGGA TACCTGTCCG CCTTTCTCCC TTCGGGAAGC GTGGCGCTTT CTCATAGCTC    6420

ACGCTGTAGG TATCTCAGTT CGGTGTAGGT CGTTCGCTCC AAGCTGGGCT GTGTGCACGA    6480

ACCCCCCGTT CAGCCCGACC GCTGCGCCTT ATCCGGTAAC TATCGTCTTG AGTCCAACCC    6540

GGTAAGACAC GACTTATCGC CACTGGCAGC AGCCACTGGT AACAGGATTA GCAGAGCGAG    6600

GTATGTAGGC GGTGCTACAG AGTTCTTGAA GTGGTGGCCT AACTACGGCT ACACTAGAAG    6660

GACAGTATTT GGTATCTGCG CTCTGCTGAA GCCAGTTACC TTCGGAAAAA GAGTTGGTAG    6720

CTCTTGATCC GGCAAACAAA CCACCGCTGG TAGCGGTGGT TTTTTTGTTT GCAAGCAGCA    6780

GATTACGCGC AGAAAAAAAG GATCTCAAGA AGATCCTTTG ATCTTTTCTA CGGGGTCTGA    6840

CGCTCAGTGG AACGAAAACT CACGTTAAGG GATTTTGGTC ATGAGATTAT CAAAAAGGAT    6900

CTTCACCTAG ATCCTTTTAA ATTAAAAATG AAGTTTTAAA TCAATCTAAA GTATATATGA    6960

GTAAACTTGG TCTGACAGTT ACCAATGCTT AATCAGTGAG GCACCTATCT CAGCGATCTG    7020

TCTATTTCGT TCATCCATAG TTGCCTGACT CCCCGTCGTG TAGATAACTA CGATACGGGA    7080

GGGCTTACCA TCTGGCCCCA GTGCTGCAAT GATACCGCGA GACCCACGCT CACCGGCTCC    7140

AGATTTATCA GCAATAAACC AGCCAGCCGG AAGGGCCGAG CGCAGAAGTG GTCCTGCAAC    7200

TTTATCCGCC TCCATCCAGT CTATTAATTG TTGCCGGGAA GCTAGAGTAA GTAGTTCGCC    7260

AGTTAATAGT TTGCGCAACG TTGTTGCCAT TGCTACAGGC ATCGTGGTGT CACGCTCGTC    7320

GTTTGGTATG GCTTCATTCA GCTCCGGTTC CCAACGATCA AGGCGAGTTA CATGATCCCC    7380

CATGTTGTGC AAAAAAGCGG TTAGCTCCTT CGGTCCTCCG ATCGTTGTCA GAAGTAAGTT    7440

GGCCGCAGTG TTATCACTCA TGGTTATGGC AGCACTGCAT AATTCTCTTA CTGTCATGCC    7500

ATCCGTAAGA TGCTTTTCTG TGACTGGTGA GTACTCAACC AAGTCATTCT GAGAATAGTG    7560

TATGCGGCGA CCGAGTTGCT CTTGCCCGGC GTCAATACGG GATAATACCG CGCCACATAG    7620

CAGAACTTTA AAAGTGCTCA TCATTGGAAA ACGTTCTTCG GGGCGAAAAC TCTCAAGGAT    7680

CTTACCGCTG TTGAGATCCA GTTCGATGTA ACCCACTCGT GCACCCAACT GATCTTCAGC    7740

ATCTTTTACT TTCACCAGCG TTTCTGGGTG AGCAAAAACA GGAAGGCAAA ATGCCGCAAA    7800

AAAGGGAATA AGGGCGACAC GGAAATGTTG AATACTCATA CTCTTCCTTT TTCAATATTA    7860

TTGAAGCATT TATCAGGGTT ATTGTCTCAT GAGCGGATAC ATATTTGAAT GTATTTAGAA    7920

AAATAAACAA ATAGGGGTTC CGCGCACATT TCCCCGAAAA GTGCCACCTG ACGTCTAAGA    7980

AACCATTATT ATCATGACAT TAACCTATAA AAATAGGCGT ATCACGAGGC CCTTTCGTCT    8040

CGCGCGTTTC GGTGATGACG GTGAAAACCT CTGACACATG CAGCTCCCGG AGACGGTCAC    8100
```

```
AGCTTGTCTG TAAGCGGATG CCGGGAGCAG ACAAGCCCGT CAGGGCGCGT CAGCGGGTGT      8160

TGGCGGGTGT CGGGGCTGGC TTAACTATGC GGCATCAGAG CAGATTGTAC TGAGAGTGCA      8220

CCATA                                                                 8225

(2) INFORMATION FOR SEQ ID NO: 2:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 2:

GCTGCAGCGA TCGCACGT                                                     18

(2) INFORMATION FOR SEQ ID NO: 3:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 3:

CATGCTGCAG CGATCGC                                                      17

(2) INFORMATION FOR SEQ ID NO: 4:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 4:

GCGATCGCTG CAGCCA                                                       16

(2) INFORMATION FOR SEQ ID NO: 5:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 5:

AGCTTCGATC GCTGCAGTCG ACTCTAGAGG ATCCCGGGCG GCCGCTGCAG CGATCGAATT       60
```